(12) United States Patent
Schechter et al.

(10) Patent No.: US 7,625,368 B2
(45) Date of Patent: Dec. 1, 2009

(54) ENDOMETRIAL ABLATION DEVICE AND METHOD

(75) Inventors: Doris Schechter, Zikhron Yakov (IL); Nir Berzak, Zikhron-Yaakov (IL)

(73) Assignee: Galil Medical Ltd., Yokneam (IL)

( * ) Notice: Subject to any disclaimer, the term of this patent is extended or adjusted under 35 U.S.C. 154(b) by 458 days.

(21) Appl. No.: 11/250,472

(22) Filed: Oct. 17, 2005

(65) Prior Publication Data

US 2007/0088344 A1   Apr. 19, 2007

(51) Int. Cl.
   *A61B 18/18* (2006.01)
(52) U.S. Cl. .......................................... 606/21; 606/23
(58) Field of Classification Search ............... 606/20–26
   See application file for complete search history.

(56) References Cited

U.S. PATENT DOCUMENTS

| 4,082,096 A | * | 4/1978 | Benson | 606/23 |
| 4,146,030 A | * | 3/1979 | Holroyd | 606/26 |
| 4,802,475 A | * | 2/1989 | Weshahy | 606/21 |
| 5,501,681 A | * | 3/1996 | Neuwirth et al. | 606/21 |
| 5,846,235 A | * | 12/1998 | Pasricha et al. | 606/23 |
| 6,547,784 B1 | * | 4/2003 | Thompson et al. | 606/21 |
| 6,551,274 B2 | * | 4/2003 | Heiner | 604/113 |
| 6,706,037 B2 | * | 3/2004 | Zvuloni et al. | 606/21 |
| 6,908,462 B2 | * | 6/2005 | Joye et al. | 606/20 |
| 7,101,367 B2 | * | 9/2006 | Xiao et al. | 606/21 |
| 2005/0177147 A1 | * | 8/2005 | Vancelette et al. | 606/21 |
| 2006/0264920 A1 | * | 11/2006 | Duong | 606/21 |
| 2008/0045934 A1 | * | 2/2008 | Schechter et al. | 606/21 |

OTHER PUBLICATIONS

International Preliminary Report on Patentability Dated Dec. 11, 2008 From the International Preliminary Examining Authority Re.: Application No. PCT/IL2006/001191.
International Search Report Dated Jun. 5, 2008 From the International Searching Authority Re.: Application No. PCT/IL2006/001191.
Written Opinion Dated Jun. 5, 2008 From the International Searching Authority Re.: Application No. PCT/IL2006/001191.

* cited by examiner

*Primary Examiner*—Michael Peffley (57) ABSTRACT

A device for uniform ablation of the endometrium comprises a transparent inflatable coolable balloon, flexible cryoprobes operable to be advanced into the uterine cornuae, an applicator operable to deliver balloon and cryoprobes to and from the uterine cavity, and optional channels for a hysteroscope and a light source, enabling observation of the uterine cavity during device insertion and observation of the endometrium during various stages of the ablation process.

19 Claims, 7 Drawing Sheets

ENDOMETRIAL ABLATION DEVICE AND METHOD

FIELD AND BACKGROUND OF THE INVENTION

The present invention relates to apparatus and methods for thermal treatment of the endometrium. More particularly, the present invention relates to an apparatus for applying ablation energies to the entire surface of the endometrium in a controlled manner. A preferred embodiment of the invention comprises an optionally transparent inflatable coolable balloon operable to cool the endometrium, cryoprobes operable to be advanced into and to cool the uterine cornuae, an applicator operable to deliver balloon and cryoprobes to and from the uterine cavity, and optional channels for a hysteroscope and a light source, enabling observation of all aspects of the ablation process. The apparatus and method are particularly useful for treatment of dysfunctional uterine bleeding.

Dysfunctional uterine bleeding (hereafter "DUB") is menstrual bleeding which deviates from normal menstrual patterns, either in the frequency of menstruation or in the duration or amount of bleeding, in the absence of pregnancy, infection, tumor or other organic lesion. DUB is reported to affect 20% of women worldwide and is even higher during adolescence and the decade preceding menopause. The most frequent cause of dysfunctional uterine bleeding is anovulation. The proportion of cases of dysfunctional uterine bleeding in the presence of ovulation is apparently very low. In the West, dysfunctional uterine bleeding is reported to be the leading cause of iron deficiency anemia.

The objective of treatment is twofold: to eliminate excessive bleeding and to improve the patient's quality of life.

The first-line treatment of dysfunctional uterine bleeding is usually medical. Hormone therapy often the basis of treatment, since in most cases the underlying cause of dysfunctional uterine bleeding is anovulation. In the absence of a causal disease in a woman who ovulates and who has dysfunctional uterine bleeding, nonsteroidal antiinflammatories (NSAIDs) and antifibrinolytics are used. Danazol and gonadoliberin agonists are used in the treatment of menstrual bleeding refractory to the other forms of medical therapy.

However, medical treatment is seldom a lasting solution to dysfunctional uterine bleeding and is not without adverse effects.

When drug therapy fails, surgical intervention is generally the next option.

Curettage stabilizes bleeding in some women, but its effects are almost never long-lasting. This procedure is therefore not recommended in the treatment of dysfunctional uterine bleeding.

Uterine artery embolization has occasionally been used for patients presenting barriers to major invasive surgery, but the long-term efficacy and safety of this surgical treatment modality have not yet been demonstrated for dysfunctional uterine bleeding.

Hysterectomy has, for many years, been the most widely used treatment for DUB. It can be performed abdominally, vaginally or laparoscopically. The vaginal and laparoscopic approaches are reported to cause fewer complications and to result in a shorter hospital stay and convalescence than the abdominal approach. However, hysterectomy is a major surgical procedure with inherent risks and the potential for complications. Although hysterectomy yields a high level of satisfaction in that it guarantees the permanent cessation of menstrual bleeding, it is a major procedure. Its invasiveness, morbidity, mortality and costs are well-known disadvantages of the procedure. In addition, hysterectomy can lead to a variety of psychological and physical changes in women. For these various reasons, other, less invasive treatments for DUB have been sought.

Endometrial ablation was adopted in clinical practice toward the end of the 1980s as a less invasive alternative to hysterectomy for treating DUB. Endometrial ablation permits preservation of the uterus and reduces uterine bleeding in most patients. Endometrial ablation is less invasive, more convenient and less expensive than hysterectomy, at least when no complicating gynecologic conditions are involved. Women with dysfunctional uterine bleeding typically prefer endometrial ablation to hysterectomy because the surgery is less invasive, involves less risk of early menopause and sexual impairment, the changes wrought are less profound, and the hospital stay and convalescence are shorter.

First-generation endometrial ablation techniques were primarily based on use of lasers or electrosurgical tools to destroy the entire thickness of the endometrium, thereby avoiding its regeneration. Such techniques are hysteroscopically assisted, with direct, real-time visual monitoring of the uterine cavity. These first-generation endometrial ablation techniques are clearly effective in treating DUB, but have the disadvantage of requiring that they be practiced by skilled operators with specialized training, and may entail surgical complications.

The first-generation techniques are usually performed under general anesthesia but can also be performed with local or regional anesthesia. They require direct visual monitoring of the uterine cavity by means of a hysteroscope and an irrigation fluid. Even if the uterine cavity appears normal on hysteroscopy, an endometrial biopsy is preferably performed because hysteroscopy alone cannot rule out the possibility of a tumor or carcinoma of the endometrium. These techniques are sometimes grouped under the heading of hysteroscopic endometrial ablation techniques. The complications associated with the first-generation ablation techniques include cervical laceration and uterine perforation, injury to the intestine by the conduction of electrical current or direct trauma, fluid overload, allergic reactions and other systemic toxic reactions caused by fluids used to distend the uterine cavity during hysteroscopy, hemorrhage if the ablation extends too deeply into the myometrium and large blood vessels are cut, and (rarely) gas embolism, an unusual but potentially fatal complication of surgical hysteroscopy. Yet these first-generation techniques offer considerable advantages over hysterectomy, in that they take less time to perform and require a much shorter hospital stay and convalescence.

First-generation endometrial ablation techniques include transcervical resection, rollerball ablation, and laser ablation. These techniques are considered to have acceptable risk levels and are currently practiced. However, each requires anesthesia, cervical dilation, and a high level of surgical skill on the part of the medical practitioner. Transcervical resection carries a risk of uterine perforation and of systemic absorption of irrigation fluid as a result of blood vessel exposure, and is contraindicated in cases of hemodynamic instability, coagulopathies, and with patients undergoing anticoagulant therapy. Rollerball ablation carries a somewhat lower risk of uterine perforation and fluid absorption, yet still requires a high level of skill and training. Laser ablation is also causes fewer intraoperative complications than transcervical resection, yet requires even more surgical skill and training, and is a lengthy and costly procedure.

A second generation of endometrial ablation techniques has been more recently developed, in quest of means to destroy the entire thickness of the endometrium while at the same time preventing the associated risks and obviating the skill requirements that the first-generation techniques described above. Most of these newer surgical techniques do not require hysteroscopy and are performed in a 'blind' manner.

Manufacturers market most second-generation techniques as procedures that can be performed on an outpatient basis. Indeed, as compared to the first-generation techniques described above, second-generation techniques are relatively faster, easier, are amenable to local anesthesia or narcosis, and cause fewer intra-operative complications. They do, however, carry risk of complications, which include hematometra, infection and internal organ injury.

Given that these new techniques are performed without visual hysteroscopic monitoring (with the exception of hydrothermal endometrial ablation), recommended treatment protocols call for visual examination, pathophysiological study including a hysteroscopy, and an endometrial biopsy prior to treatment. It is also recommended to perform a hysteroscopy after the treatment to check that only the uterine cavity was treated.

Second-generation ablation techniques include thermal balloon ablation, microwave ablation, hydrothermal ablation, impedance-controlled ablation, and cryoablation. While presenting advantages of simplicity when compared to hysterectomy and first-generation ablation techniques, each of these second-generation techniques presents specific limitations and disadvantages.

Thermal balloon ablation is only appropriate for wholly normal uterine cavities. Uterine retroversion and irregularities of the uterine cavity appear to be associated with a greater risk of treatment failure. The treatment is contraindicated in presence of active genital or urinary tract infection and of any anatomic abnormality or any disease that can cause myometrial weakening. In addition, the treatment causes pain due to uterine distention.

Microwave ablation is also appropriate only for the well-formed uterus, because microwave endometrial ablation tends to be incomplete in women whose uterine cavity is hypertrophied or highly deformed. Microwave ablation is also painful, because the cervix must be dilated to 9 mm in order to insert the microwave waveguide, and that dilatation process can be painful even under local anesthesia.

Hydrothermal ablation requires prior diagnostic hysteroscopy to check that there are no uterine perforations and to detect any intrauterine conditions that were not previously diagnosed. It is important to carefully select candidates for this operation, since a large submucosal leiomyoma deforming the uterine cavity will prevent adequate irrigation. Hydrothermal endometrial ablation is contraindicated in presence of active genital or urinary tract infection and of any anatomic abnormality, condition or previous intervention that can cause myometrial weakening, such as a classic cesarean section or a previous transmural myomectomy. Hydrothermal ablation also is painful, in that it requires the cervix be dilated to 8 mm in order to insert the ablation device, and that dilatation process can be painful even under local anesthesia.

Impedance-controlled ablation offers the advantage of not requiring preoperative endometrial thinning. This procedure can be performed at any time during the menstrual cycle, even during menstruation. Impedance-controlled endometrial ablation is contraindicated in the presence of an active genital or urinary tract infection and any anatomic abnormality, any condition or any intervention that can cause myometrial weakening, such as a classic cesarean section or a previous transmural myomectomy. Furthermore, if the uterine cavity is less than 4 cm in length, the treatment will cause burning of the walls of the cervix. It should be noted that the cervix has to be dilated to 8 mm in order to insert the device and that the dilatation process can be painful, even with local anesthesia.

Endometrial cryoablation has typically be performed either by utilizing a single cryoprobe sequentially displaced to and operated at two or more ablation sites during a surgical procedure, or by utilizing up to three independent cryoprobes inserted simultaneously in a uterus, for example, one in the uterine cavity and one in each of the cornua, and using sonography to confirm that the cryosurgical devices are properly positioned in the uterine cavity and to monitor the growth of the ice crystal during the treatment cycles. Cryoablation utilizing these prior art methods has the disadvantage that ablation is not well controlled in that cold is not and cannot be evenly distributed over the endometrial surface, and that the condition of the endometrial surface cannot be observed and evaluated during the cryoablation procedure.

To summarize, it has been seen that some prior art techniques are highly invasive, that other prior art techniques are less highly invasive but are likely to entail surgical complications and require highly skilled operators with specialized training. Therefore there is a widely felt need for, and it would be highly advantageous to have, an apparatus and technique for endometrial ablation which is minimally invasive and does not require highly skilled operators and specialized training.

Further, it has been seen that recently developed endometrial ablation techniques are of limited applicability for use in uterine cavities which are not entirely regular and well formed. The various second-generation techniques tend to be inappropriate for patients having a uterus which is asymmetrical, or which has malformations or large growths, or dissimilar uterine cornuae. Yet, very many patients present a uterine topography which varies from the ideal norm. Thus, there is a widely felt need for, and it would be highly advantageous to have, an apparatus and technique for endometrial ablation operable to treat a wide variety of uterine forms, including asymmetrical forms, those comprising dissimilar uterine cornuae, and those including internal growths and irregularities of the uterine cavity.

It has also been seen that most second-generation endometrial ablation procedures are painful. In particular, most such procedures require anesthesia during performance of the ablative process, and therefore are of limited applicability in simpler clinical settings. Thus, there is a widely felt need for, and it would be highly advantageous to have, an apparatus and technique for endometrial ablation which does not require severe distension of the uterus during treatment, does not require pronounced cervical dilation to permit introduction of an ablative instrument into the uterus. In general, there is a widely felt need for, and it would be highly advantageous to have, an apparatus and technique for endometrial ablation which is not painful, does not require anesthesia during treatment, and which therefore is appropriate for use in an "office visit" setting.

It has further been seen that prior art cryoablation techniques to not provide well controlled and/or uniform application of cold to the entire endometrial surface. Thus, there is a widely felt need for, and it would be highly advantageous to have, an apparatus and technique for endometrial cryoablation able to provide a well-controlled energy transfer uniformly over the entire surface of the endometrium, and which provides means for observing and assessing the condition of the endometrium before, during, and after cryoablation.

SUMMARY OF THE INVENTION

According to one aspect of the present invention there is provided a device for thermal treatment of the endometrium, comprising (a) a flexible inflatable coolable balloon which comprises two conduits for ablative probes, the balloon is shaped to contact an endometrium of a uterus when the balloon is inflated within a uterus; (b) two flexible cryoprobes operable to be positioned within the conduits; and (c) an applicator operable to contain the balloon and the probes during insertion of the device into a uterus.

In a preferred embodiment the balloon is operable to extend from the applicator when the applicator is inserted in a uterus, and operable to be inflated and cooled within that uterus, and thereby to cryoablate endometrial tissue within the uterus. The balloon may comprise a cryogenic fluid input lumen and a cryogenic fluid exhaust lumen. Alternatively, the balloon comprises a third cryoprobe conduit enabling to insert a cryoprobe into an interior volume of the balloon, and further comprises a thermal transfer medium lumen through which a thermal transfer medium may be inserted into the balloon, thereby inflating the balloon. An inserted cryoprobe within the balloon volume can then cool the endometrium by thermal transfer through the thermal transfer medium filling the balloon and through the balloon walls.

According to further features in preferred embodiments of the invention described below, the cryoprobes are operable to be extended from the conduits into uterine cornuae when the device is inserted in a uterus, and further operable to cryoablate endometrial tissue within the cornuae. In a preferred embodiment, at least one of the cryoprobes comprises shape memory metal.

According to yet further features in preferred embodiments of the invention described below, the balloon is transparent and the device comprises a channel for inserting a hysteroscope into the transparent balloon, thereby enabling a user to observe portions of the endometrium through the transparent balloon. Preferably the device comprises a channel for a light source, a hysteroscope, and a light source.

According to yet further features in preferred embodiments of the invention described below, the device further comprises a pressure sensor operable to report pressure within the inflatable balloon during inflation of the balloon, and a temperature sensor on a surface of the balloon.

According to another aspect of the present invention there is provided a method for endometrial ablation, comprising (a) providing an endometrial ablation device which comprises an inflatable balloon and two ablation probes contained within an applicator; (b) inserting the applicator through a cervix into a cavity of a uterus; (c) pushing the balloon and the cryoprobes from the inserted applicator into the uterine cavity; (d) inflating the balloon so that the balloon contacts the endometrium of the uterus; (e) advancing the cryoprobes into cornuae of the uterus; (f) cooling the balloon to treat endometrial tissue of the uterine cavity, and cooling the cryoprobes to treat endometrial tissue of the cornuae; (g) deflating the balloon; (h) retracting the cryoprobes and the balloon into the applicator; and (i) extracting the applicator, containing the balloon and the cryoprobes, from the uterus.

According to yet further features in preferred embodiments of the invention described below, the inflatable balloon is transparent, and the method further comprises inserting a viewing optic of a hysteroscope into the transparent balloon when the transparent balloon is inserted in a uterine cavity, observing endometrial tissue through the transparent balloon, observing at least one of the cryoprobes through the hysteroscope while guiding the observed cryoprobe towards and into a uterine cornua, and utilizing the hysteroscope to assess condition of endometrial tissue subsequent to cooling of the tissue by the device.

The present invention successfully addresses the shortcomings of the presently known configurations by providing an apparatus and technique for endometrial ablation which is neither highly invasive nor highly dangerous, and which does not require highly skilled operators with specialized training for its operation.

The present invention further successfully addresses the shortcomings of the presently known configurations by providing an apparatus and technique for endometrial ablation operable to treat a wide variety of uterine forms, including asymmetrical forms, forms comprising dissimilar uterine cornuae, and forms including internal growths and irregularities of the uterine cavity. The invention in particular provides means for individual control of treatment of each uterine cornua, providing appropriate treatment despite cornual dissimilarities.

The present invention yet further successfully addresses the shortcomings of the presently known configurations by providing an apparatus and technique for endometrial ablation which does not require severely distend the uterus during treatment and does not require pronounced cervical dilation to introduce an ablative instrument into the uterus.

The present invention yet further successfully addresses the shortcomings of the presently known configurations by providing an apparatus and technique for endometrial ablation which is not painful, does not require anesthesia during treatment, and which can therefore be applied in an "office visit" clinical setting.

The present invention yet further successfully addresses the shortcomings of the presently known configurations by providing an apparatus and technique for endometrial cryoablation able to provide a well-controlled energy transfer uniformly over the entire surface of the endometrium, and further providing means for observing and assessing the condition of the endometrium before, during, and after cryoablation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of devices and methods for thermal ablation of the endometrium as treatment for dysfunctional uterine bleeding and related conditions. Specifically, devices and methods here disclosed enable application of ablation energies to the entire surface of the endometrium in a controlled and uniform manner.

A preferred embodiment of the present invention comprises a transparent inflatable coolable balloon operable to cool the endometrium, cryoprobes operable to be advanced into the uterus cornuae for cooling endometrial tissues therein, an applicator operable to deliver balloon and cryoprobes to and from the uterine cavity, and optional channels within balloon and applicator for a hysteroscope and a light source, enabling observation of all aspects of the ablation process.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

To enhance clarity of the following descriptions, the following terms and phrases will first be defined:

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

The phrase "Joule-Thomson heat exchanger" as used herein refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice, referred to herein as a "Joule-Thomson orifice", through which gas passes from the first, higher pressure, region of the device to the second, lower pressure, region of the device. A Joule-Thomson heat exchanger may further include a heat-exchanging configuration, for example a heat-exchanging configuration used to cool gasses within a first region of the device, prior to their expansion into a second region of the device.

The phrase "cooling gasses" is used herein to refer to gasses which have the property of becoming colder when passed through a Joule-Thomson heat exchanger. As is well known in the art, when gasses such as argon, nitrogen, air, krypton, $CO_2$, $CF_4$, and xenon, and various other gasses pass from a region of higher pressure to a region of lower pressure in a Joule-Thomson heat exchanger, these gasses cool and may to some extent liquefy, creating a cryogenic pool of liquefied gas. This process cools the Joule-Thomson heat exchanger itself, and also cools any thermally conductive materials in contact therewith. A gas having the property of becoming colder when passing through a Joule-Thomson heat exchanger is referred to as a "cooling gas" in the following.

The phrase "heating gasses" is used herein to refer to gasses which have the property of becoming hotter when passed through a Joule-Thomson heat exchanger. Helium is an example of a gas having this property. When helium passes from a region of higher pressure to a region of lower pressure, it is heated as a result. Thus, passing helium through a Joule-Thomson heat exchanger has the effect of causing the helium to heat, thereby heating the Joule-Thomson heat exchanger itself and also heating any thermally conductive materials in contact therewith. Helium and other gasses having this property are referred to as "heating gasses" in the following.

As used herein, a "Joule Thomson cooler" is a Joule Thomson heat exchanger used for cooling. As used herein, a "Joule Thomson heater" is a Joule Thomson heat exchanger used for heating.

The terms "ablation temperature" and "cryoablation temperature", as used herein, relate to the temperature at which cell functionality and structure are destroyed by cooling. According to current practice temperatures below approximately $-40°$ C. are generally considered to be ablation temperatures.

As used herein, the term "high-pressure" as applied to a gas is used to refer to gas pressures appropriate for Joule-Thomson cooling of cryoprobes. In the case of argon gas, for example, "high-pressure" argon is typically between 3000 psi and 4500 psi, though somewhat higher and lower pressures may sometimes be used.

It is expected that during the life of this patent many relevant cryoprobes and inflatable uterine balloons will be developed, and the scope of the terms "cryoprobe" and "balloon" are intended to include all such new technologies a priori.

As used herein the term "about" refers to ±10%.

In discussion of the various figures described hereinbelow, like numbers refer to like parts.

Figure 1:
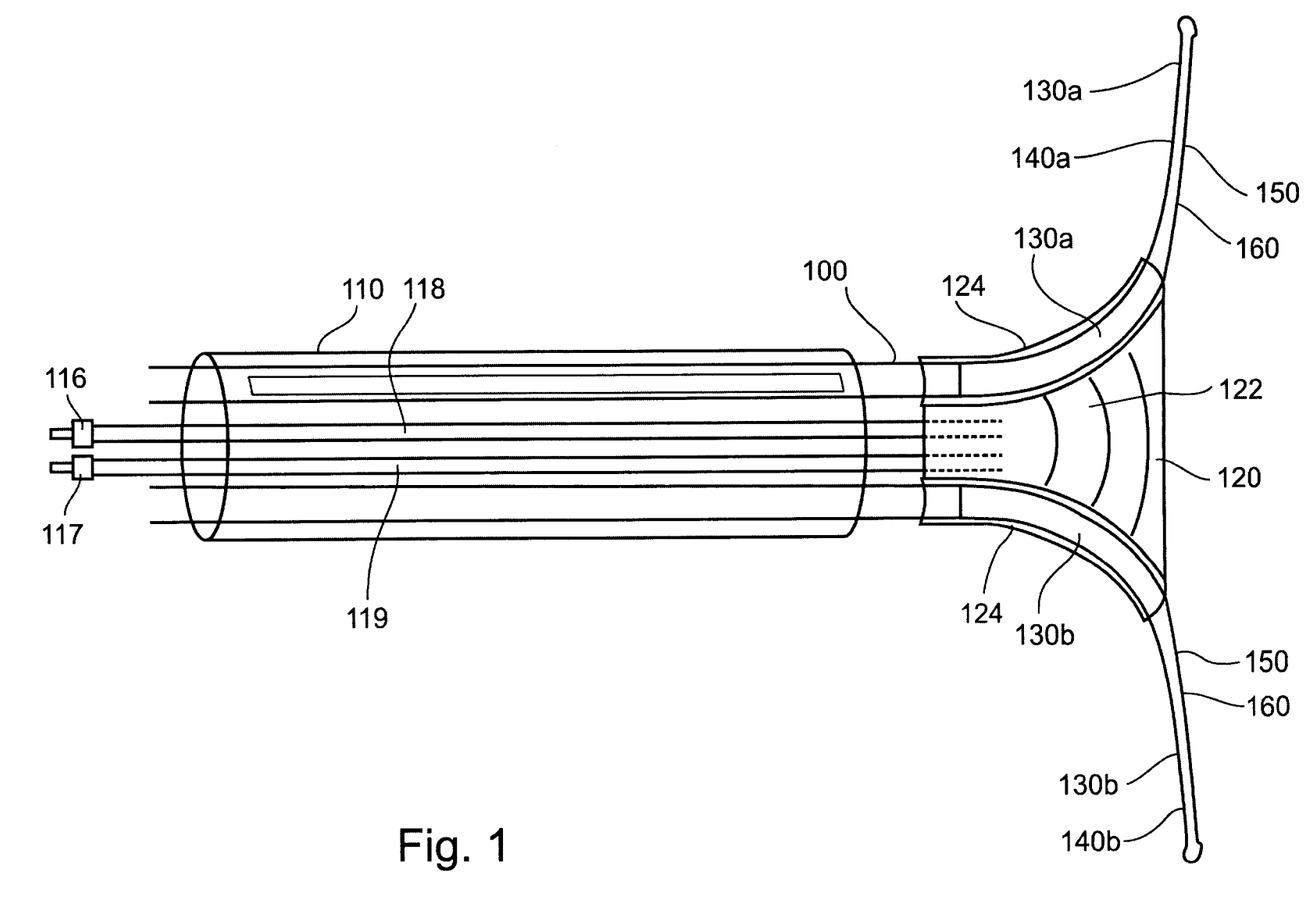
FIG. 1 is a simplified schematic of an endometrial ablation device in fully opened position, according to an embodiment of the present invention.

Attention is now directed to FIG. 1, which presents a simplified schematic of an endometrial ablation device according to an embodiment of the present invention. Device 100 comprises an applicator 110 (also referred to as introducer 110), a pliable inflatable balloon 120, and two extendable ablation probes 130a and 130b, referred to collectively as probes 130.

Balloon 120 is an inflatable compliant balloon shaped to conform, when inflated, to the shape of a uterine cavity. Balloon 120 comprises a closed inflatable volume 122 and two conduits 124, one on each side of inflatable volume 122. Conduits 124 are formed to accommodate ablation probes 130.

Ablation probes 130 are preferably cryoprobes, referred to herein as cryoprobes 140A and 140B and referred to collectively as cryoprobes 140, yet probes 130 may alternatively be other forms of ablative probes.

Figure 2:
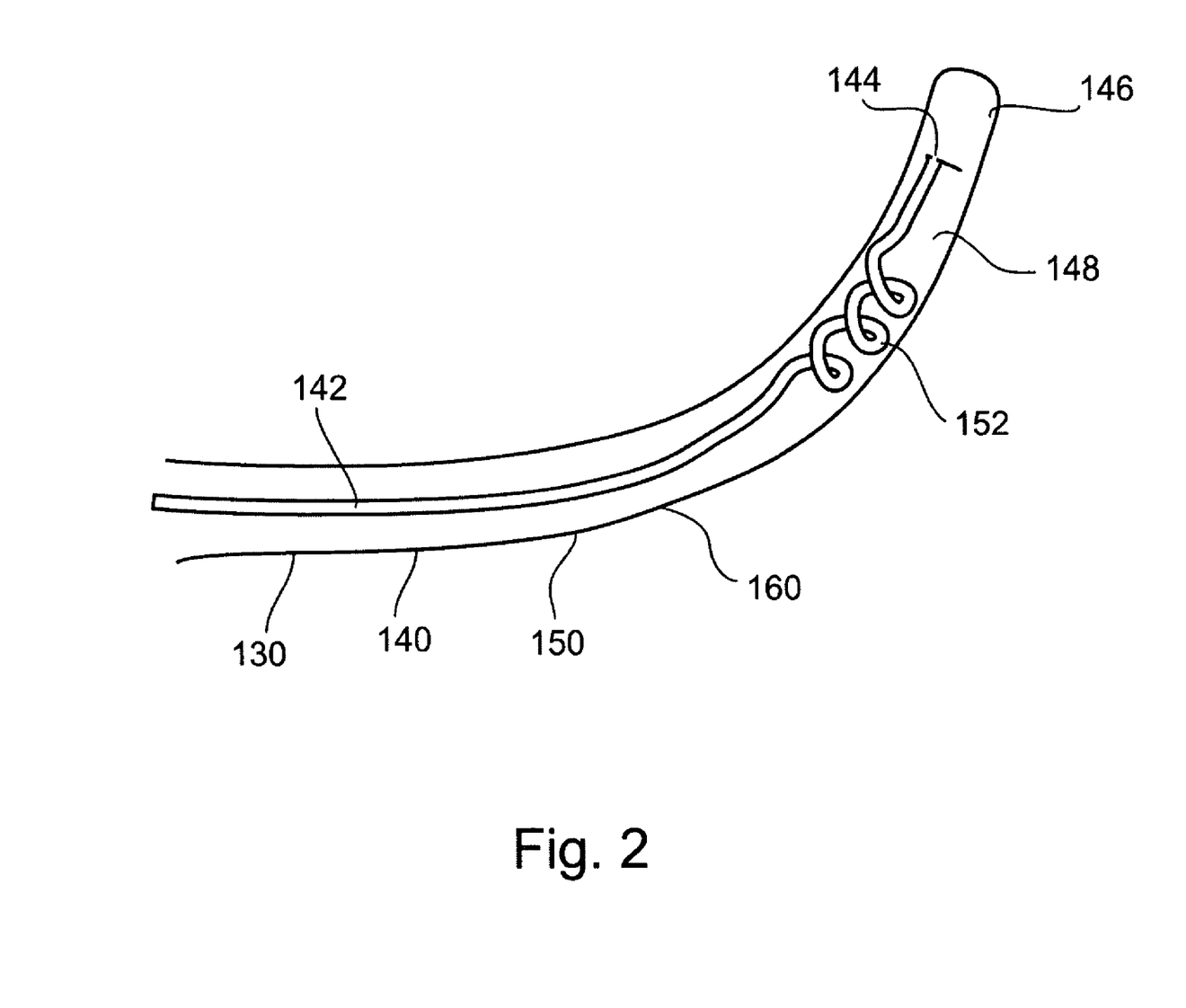
FIG. 2 is a simplified schematic of a cryoprobe component of an endometrial ablation device, according to an embodiment of the present invention.

Attention is now drawn to FIG. 2, which presents a simplified schematic of a cryoprobe appropriate for use with device 100, according to an embodiment of the present invention. Since cryoprobe technology is well known in the art, no attempt has been made to present cryoprobes 140 in detail. Cryoprobes 140 are most preferably a Joule-Thomson cryoprobes 150, though evaporative cryoprobes 160 operative to cool by evaporation of a liquefied gas may also be used. As may be seen in FIG. 2, a cryoprobe 140 comprises a fluid input lumen 142 for delivering a fluid to an expansion chamber 146, wherein a fluid delivered through input lumen 142 expands, cooling expansion chamber 146, and is then exhausted through a fluid exhaust lumen 148. If cryoprobe 140 is an evaporative cryoprobe 160, a cooling fluid such as liquefied N2O or CO2 is delivered through input lumen 142, evaporates, and expands in expansion chamber 146. If cryoprobe 140 is a Joule-Thomson cryoprobe 150, a high-pressure cooling gas such as argon is delivered through fluid input lumen 142. If cryoprobe 140 is a Joule-Thomson cryoprobe 150, a Joule-Thomson orifice 144 is provided between fluid input lumen 142 and expansion chamber 146 for regulating expansive decompression of high-pressure cooling gas from fluid input lumen 142 into expansion chamber 146. In preferred embodiments, Joule-Thomson cryoprobe 150 is designed and constructed so that at least a portion of gas input lumen 142 is positioned within or contiguous to gas exhaust lumen 148, thereby constituting a heat-exchanging configuration 152 proximal to expansion chamber 146. Heat-exchanging configuration 152 is provided to increase efficiency of Joule-Thomson cooling within probe 150, by pre-cooling gas transiting lumen 142 towards expansion chamber 146 by thermal exchange with cold gasses exhausting from expansion chamber 146 through fluid exhaust lumen 148. Heat-exchanging configuration 152 may include spiral windings, heat-conducting flanges, or other configurations designed to enhance heat transfer between gas input lumen 142 and gas exhaust lumen 148.

Referring again to FIG. 1, ablation probes 130 are sized and shaped to fit within conduits 124 of balloon 120. Probes 130 (whether these are cryoprobes 140 or other types of ablation probes) are made of a flexible yet resistant material, and are designed so they that respond to forward pressure applied to their proximal portions by advancing through conduits 124, to extend beyond conduits 124. Balloon 120 and conduits 124 are shaped so that, when device 100 is appropriately positioned within a uterus, they guide probes 130 towards the uterine cornuae. Thus device 100 is designed and configured so that probes 130 can be pushed forward through conduits 124 and beyond conduits 124, so that they advance into the uterine cornuae up to the orifices of the ovarian tubes, and are therefore positioned to be in contact with, and to ablate, the cornualendometrium.

Probes 130 are preferably constructed of MRI-compatible materials, and have blunt distal tips to minimize danger of perforation or other damage to uterine walls by pressure exerted when probes 130 are extended into the cornuae.

Figure 3:
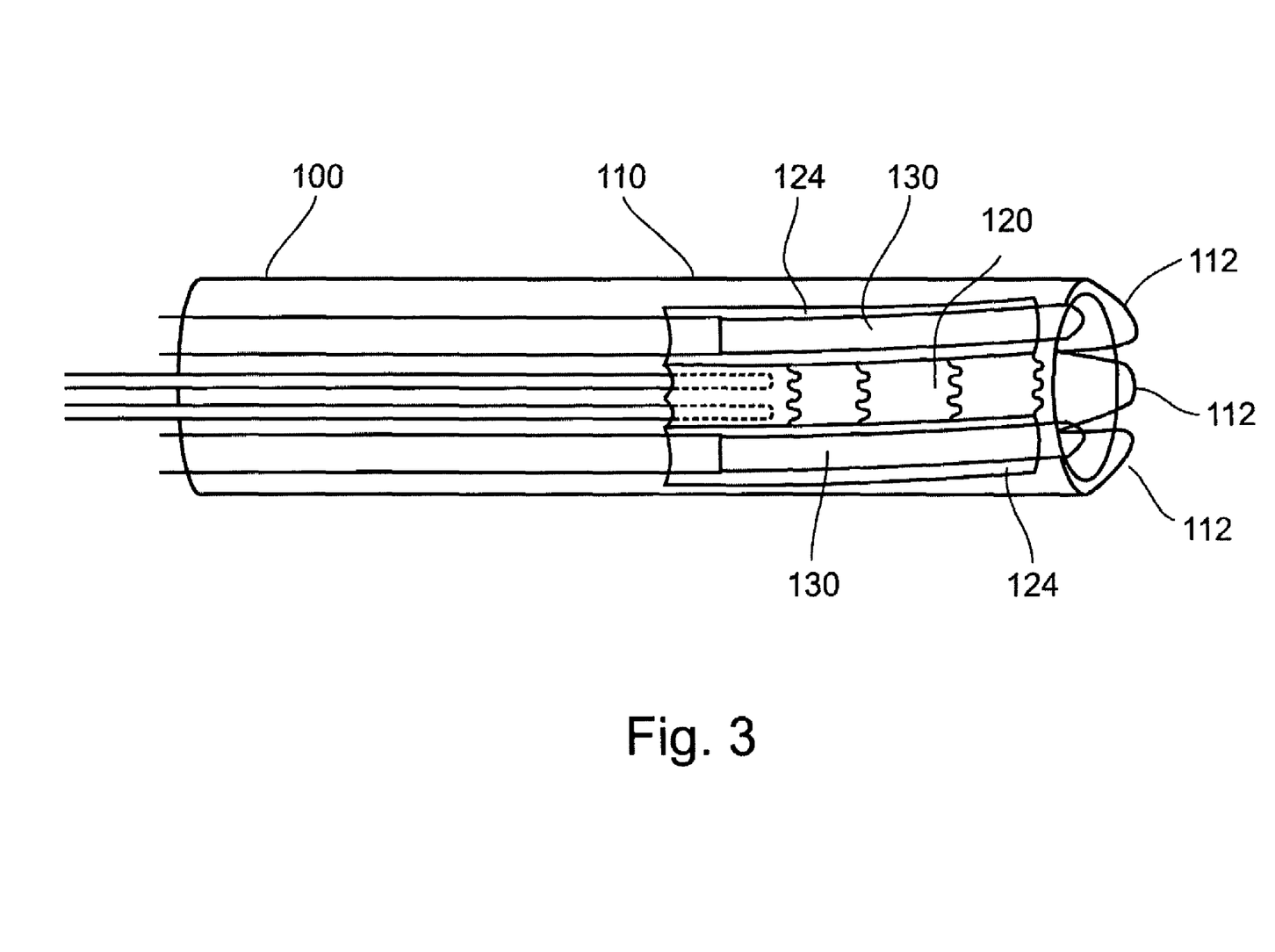
FIG. 3 is a simplified schematic of an endometrial ablation device collapsed within its applicator shell, according to an embodiment of the present invention.

Attention is now drawn to FIG. 3, which is a simplified schematic of endometrial ablation device 100 collapsed within an (optional) applicator shell 110, according to an embodiment of the present invention. Applicator 110 is designed to hold probes 130 in a compact configuration, preferably straight, and to hold deflated balloon 120 in compact format. Applicator 110 thus presents a size and shape appropriate for penetration through the cervix of a patient without requiring dilation of that cervix, or requiring only minimal dilation of the cervix. Applicator 110 is thus operable to introduce probes 130 and expandable balloon 120 into the uterine cavity. Applicator 110 is made of rigid or semi-rigid material, and preferably comprises a distal tip with two or more (optional) leaf-like valves 112 closing the distal aperture of the applicator 110, to allow safe and smooth insertion of applicator 110 through the cervix into the uterine cavity. Flexibility of probes 130 and of (deflated) balloon 120 allows these components to conform to a shape and compact size imposed by applicator 110, which shape and size are appropriate for insertion through the cervix.

After applicator 110 has been advanced into the uterine cavity, flexible leaf-like valves 112 (if present) are pushed open, allowing further advancement of the balloon/probes combination.

Figure 4:
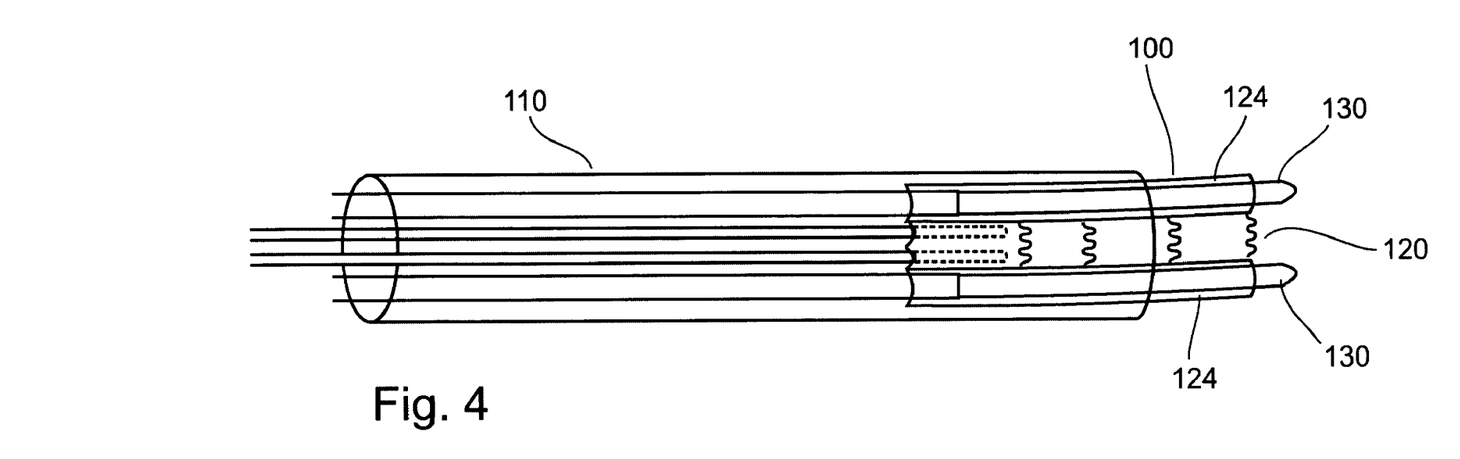
FIG. 4 is a simplified schematic of an endometrial ablation device showing an early phase of introduction of the device into the endometrium, internal components of the device having been pushed forward to emerge from the applicator, according to an embodiment of the present invention.
Figure 5:
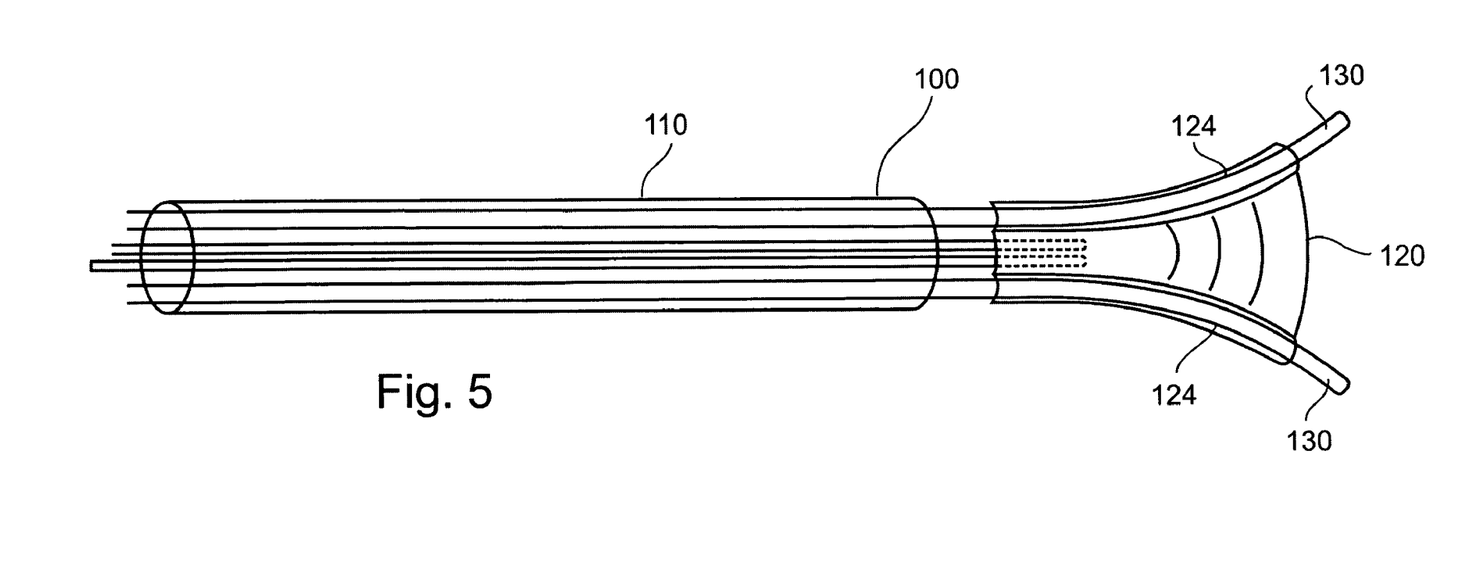
FIG. 5 is a simplified schematic of an endometrial ablation device showing a later phase of introduction of the device into the endometrium, internal components of the device having been pushed further forward to emerge from the applicator, according to an embodiment of the present invention.

Attention is now drawn to FIGS. 4 and 5, which are simplified schematics presenting stages in utilization of device 100, according to an embodiment of the present invention. Once applicator 110 has been appropriate positioned within a uterus, optional leaf-like valves 112 (if present) are pushed open as internal components balloon 120 and probes 130 of device 100 are pushed out of applicator 110 and further advanced into the uterus. FIGS. 4 and 5 show successive stages of this advancement of internal components out of applicator 110 and into the uterus. FIG. 1, discussed above, shows a final stage of insertion of device 100, wherein balloon 120 is fully inserted and probes 130 have been further extended beyond conduits 124 of balloon 120 and into the uterine cornuae.

Referring again to FIG. 1, balloon 120 may be seen to have a triangle-like shape designed to approximate the internal shape of the uterine cavity. Balloon 120 is preferably constructed of PVC, silicon, nylon, or a similar very compliant material, so as to allow free expansion of balloon 120, allowing balloon 120 to adapt to the shape of the uterine cavity into which it is inserted and within which it is expanded. Thus balloon 120 is adaptable even to irregularly shaped uterine cavities.

Balloon 120 is provided with an inflation lumen 118 through which a fluid (liquid or gas) may be introduced into balloon 120, causing balloon 120 to expand and thereby to come into close contact with the uterine cavity endometrium. Flexibility of balloon 120 is preferably such as to allow substantial contact between balloon 120 and the uterine cavity wall, even in cases of irregularity of the uterine cavity, such as may be caused by uterine malformations (e.g., uterine septum), submucosal fibroids, or similar causes of irregularity.

Balloon 120 is preferably provided with an inflation lumen 118 and an exhaust lumen 119. Balloon 120 is designed for cooling as well as for expansion. Thus, inflation lumen 118 of balloon 120 may be used to inflate balloon with a cryogenic fluid (expanded high-pressure gas or expanding evaporated liquefied gas), thereby inflating balloon 120 and expanding it as well. Cooled and inflated balloon 120 is thus operable to cool and ablate the uterine endometrium. Balloon 120 is thus preferably constructed of a material providing good thermal transmission through its walls. Balloon fluid input lumen 118 may be provided with a fluid input control valve 116 and/or balloon fluid exhaust lumen 119 may be provided with a fluid exhaust control valve 117, enabling to maintain a desired level of circulation of a coolant through balloon 120 while maintaining a desired inflation pressure within balloon 120.

Figure 6:
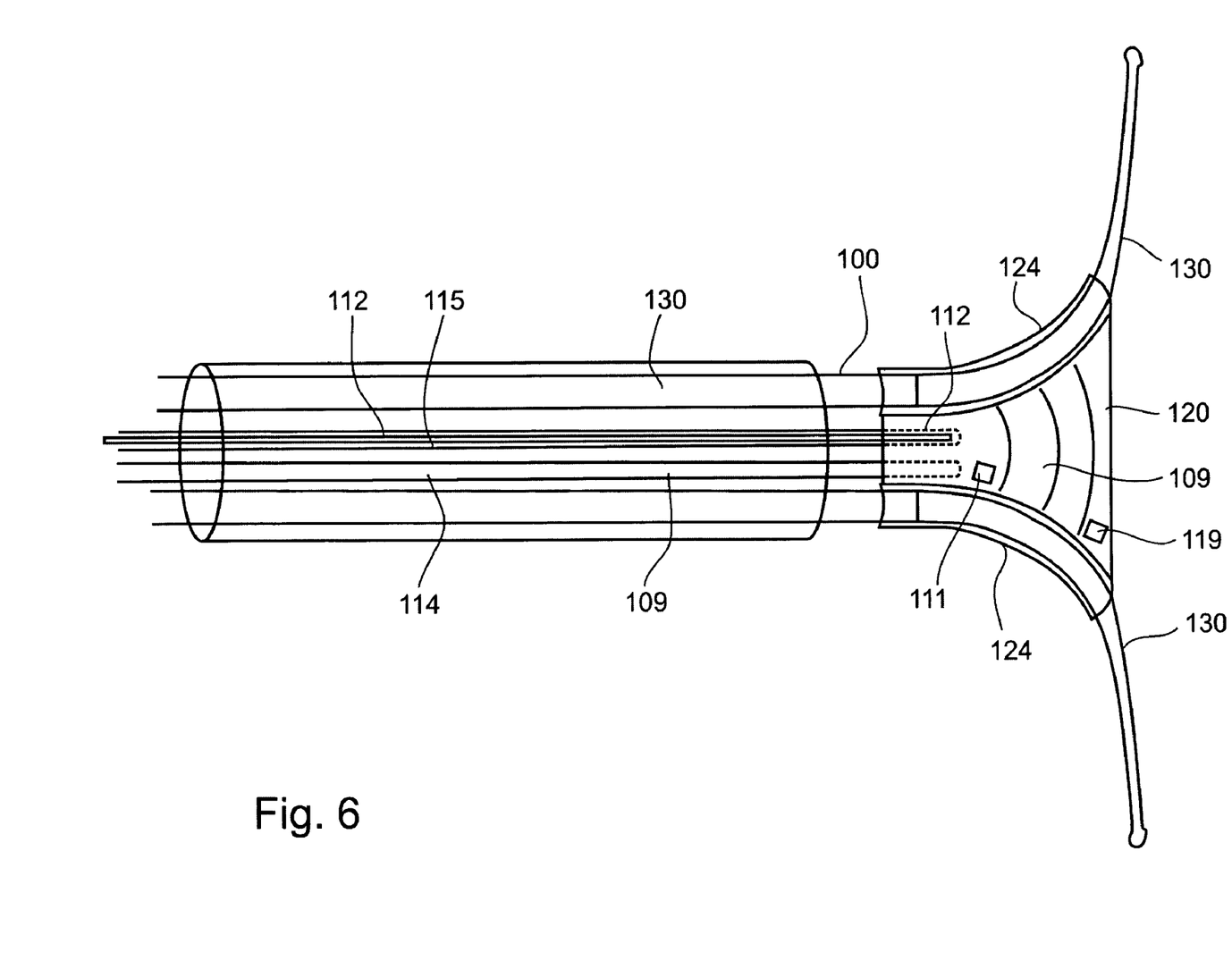
FIG. 6 is a simplified schematic of an alternative configuration of an endometrial ablation device, according to an embodiment of the present invention.

Attention is now drawn to FIG. 6, which is a simplified schematic of an alternative configuration of device 100. FIG. 6 is similar to FIG. 1, with the difference that in the embodiment presented by FIG. 6, balloon 120 is provided with an additional cryoprobe conduit 115 and a thermal transfer medium lumen 114. In this alternative embodiment, balloon 120 may be expanded by insertion therein of a fluid thermal transfer medium 109 provided through thermal transfer medium lumen 114. Medium 109 is preferably saline, gel, or any other water-based medium.

Inserted fluid thermal transfer medium 109, having inflated balloon 120, can then be cooled by cooling a cryoprobe 112 inserted through cryoprobe conduit 115 into balloon 120. Cryoprobe 112 can thus be used to cool the endometrium by heat transfer through thermal transfer medium 109 filling balloon 120 and establishing thermal contact between cryoprobe 112, thermal transfer medium 109, walls of balloon 120, and endometrium. The amount of the fluid thermal transfer medium to be inserted in balloon 120 depends upon the volume to be filled in order to achieve good contact between balloon 120 and the endometrium. A pressure sensor 111 can provide a useful feedback mechanism for controlling the inflation process, since as inflation continues, pressure within balloon 120 will rise when good contact between balloon and the endometrium has been established.

Thermal sensors 119 may be provided for monitoring temperatures at the surface of balloon 120.

Conduits 124 and the remainder of the body of balloon 120 may be made of a same material. However, in a preferred embodiment, ablation probes 130 are constructed of Nitinol or a similar material, and therefore have a shape memory. In this embodiment conduits 124 are preferably made of a material more rigid than that used to construct the central portion of balloon 120. These somewhat stiffer conduits are appropriate for holding probes 130 substantially straight prior to their release from conduits 124 towards the cornuae. When probes 130 constructed of shape memory metal are pushed forward out of conduits 124, they tend to bend according to a pre-designed curvature, giving them a shape optimally suited for advance into the tubal cavity of the cornuae, thus enhancing contact between probes 130 and the endometrium at the junction between the uterine cornuae and the ovarian tubes. As discussed, distal ends of probes 130 are preferably blunt, so as to minimize danger of perforation or damage that might be caused by probes 130 as they advance into the cornuae.

Device 100 may be designed and used as a single use device. Alternatively, balloon 120 may be a single use device while probes 110 may be constructed of reusable materials and be sterilized for re-use. Further alternatively, reusable probes 130 may be inserted for use into a single use probe cover made of a flexible and high conductive plastic material (not shown in the figure).

Figure 7:
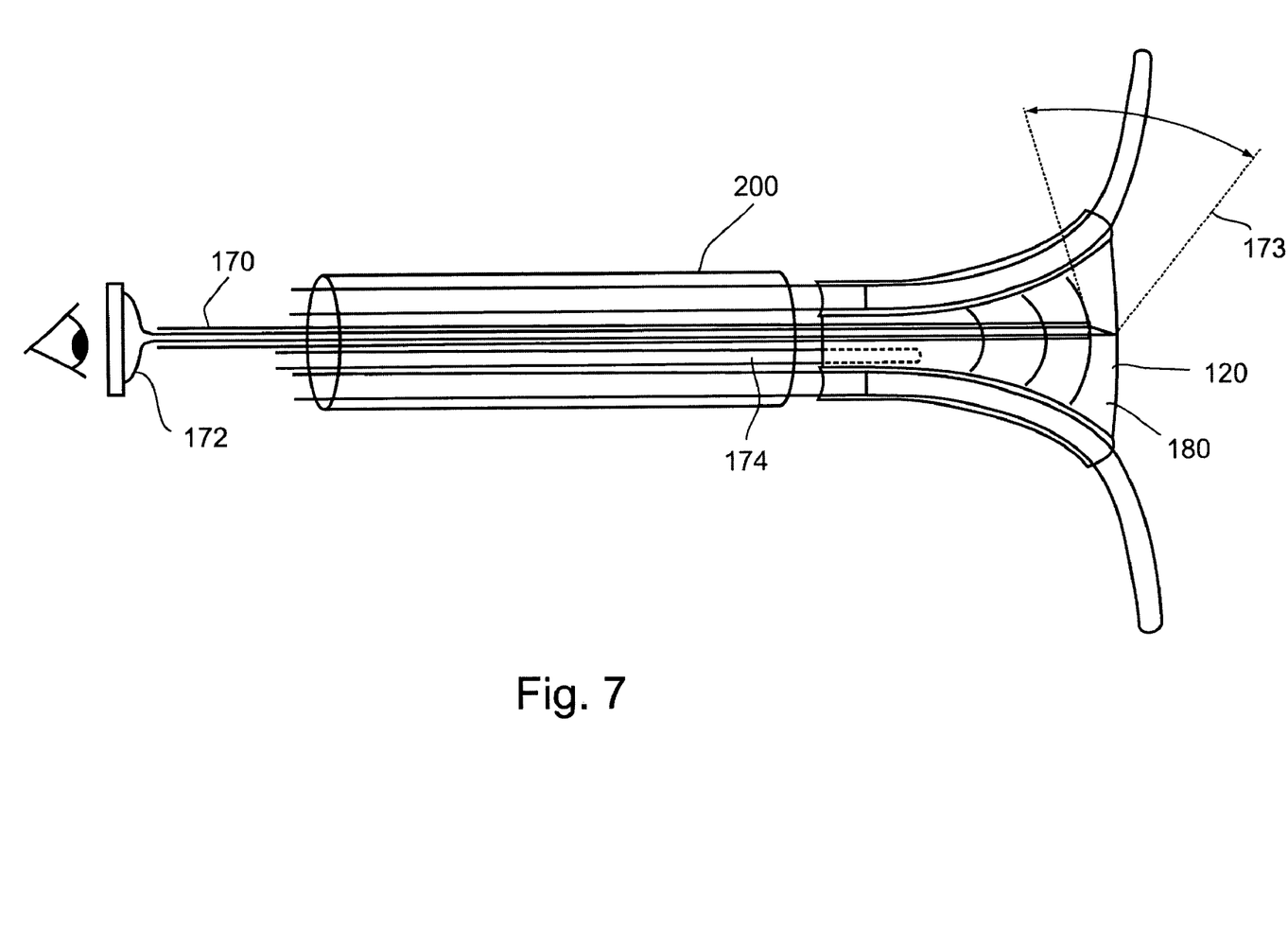
FIG. 7 is a simplified schematic of an embodiment of an endometrial ablation device comprising a channel for a hysteroscope, according to an embodiment of the present invention.

Attention is now drawn to FIG. 7, which is a simplified schematic of an embodiment of a device 200, similar to device 100 but additionally comprising a hysteroscope channel 170 through which a portion of an hysteroscope 172 may be inserted into balloon 120. Hysteroscope 172 preferably has an angular view field, designated 173 in FIG. 7. In an embodiment shown in FIG. 7, balloon 120 is constructed as a transparent balloon 180 constructed of transparent material. In this embodiment hysteroscope 172 (or balloon 180) is provided with a light channel 174, enable to provide light for viewing to the interior of the uterine cavity. (For clarity of the FIG. 7, lumens and components for inflation and cooling of balloon 180 are not presented in FIG. 7. They are to be understood to be as described hereinabove with respect to FIGS. 1 and 6.)

Figure 8:
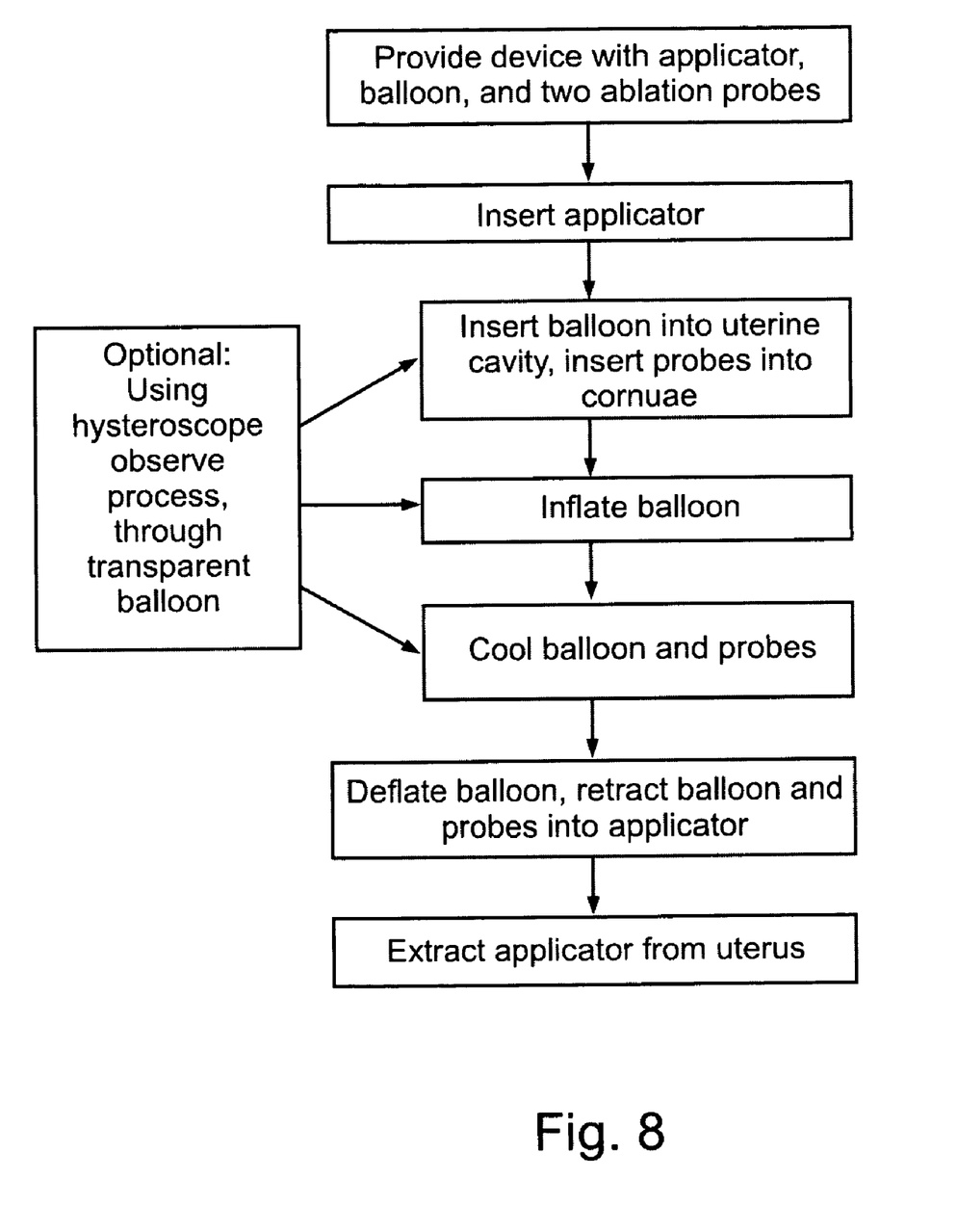
FIG. 8 is a simplified flow chart of a method for endometrial ablation, using devices presented in FIGS. 1-7, according to an embodiment of the present invention.

Attention is now drawn to FIG. 8, which is a simplified flow chart of a procedure for endometrial ablation, according to an embodiment of the present invention. As shown in FIG. 8, a procedure for endometrial ablation comprises the steps of providing an endometrial ablation device which comprises an expandable balloon and two ablation probes contained within an applicator, inserting the applicator through the cervix into the uterus (preferably up to the uterine fundus), pushing balloon and cryoprobes out of the applicator and into the uterine cavity, inflating the balloon until it contacts the endometrium, further advancing the cryoprobes until they enter the uterine cornuae, cooling balloon and cryoprobes to treat the endometrium surface including the cornuae, deflating the balloon, retracting cryoprobes and balloon into the applicator shell, and extracting the applicator with its enclosed balloon and cryoprobes from the uterus through the cervix. A preferred embodiment of the method, utilizing device 200 presented in FIG. 6, comprises utilizing hysteroscope 172 to examine the uterine cavity prior to extension of probes 130 towards the cornuae and to guide movement of probes 130 towards and into the cornuae, using hysteroscope 172 to examine the endometrium during the treatment process, and using hysteroscope 172 to assess the state of the uterine cavity and the extent of the ablated surface subsequent to ablative treatment, prior to retraction of device 200 from the uterus.

Standard imaging modalities (e.g., ultrasound, CT, MRI) may also be used during the procedures presented in FIG. 7, to monitor the various steps in the described procedure and in particular to monitor the various steps in the insertion of device 100 and its components and to verify accurate positioning thereof prior to ablation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for thermal treatment of the endometrium, comprising
   (a) a flexible inflatable coolable balloon which comprises two conduits for ablative probes, said balloon is shaped to contact an endometrium of a uterus when said balloon is inflated within said uterus;
   (b) two flexible cryoprobes operable to be positioned within said conduits, each of said cryoprobes comprising a cryogen supply lumen, an expansion chamber, and a cryogen exhaust lumen; and
   (c) an applicator operable to contain said balloon and said probes during insertion of said device into a uterus.

2. The device of claim 1, wherein said balloon is operable to extend from said applicator when said applicator is inserted in said uterus.

3. The device of claim 2, wherein said balloon is operable to be inflated and cooled within said uterus, and thereby to cryoablate endometrial tissue within said uterus.

4. The device of claim 3, wherein said balloon comprises a cryogenic fluid input lumen and a cryogenic fluid exhaust lumen.

5. The device of claim 3, wherein said balloon comprises a third cryoprobe conduit enabling to insert a cryoprobe into an interior volume of said balloon, and further comprises a thermal transfer medium lumen through which a thermal transfer medium may be inserted into said balloon, thereby inflating said balloon.

6. The device of claim 1, wherein said cryoprobes are operable to be extended from said conduits into uterine cornuae when said device is inserted in said uterus, and said cryoprobes are further operable to cryoablate endometrial tissue within said cornuae.

7. The device of claim 1, wherein at least one of said cryoprobes comprises shape memory metal.

8. The device of claim 1, wherein said balloon is transparent.

9. The device of claim 8, wherein said device comprises a channel for inserting a hysteroscope into said transparent balloon, thereby enabling a user to observe portions of said endometrium through said transparent balloon.

10. The device of claim 8, further comprising a channel for a light source.

11. The device of claim 8, further comprising a hysteroscope and a light source.

12. The device of claim 1, further comprising a pressure sensor operable to report pressure within said inflatable balloon during inflation of said balloon.

13. The device of claim 1, further comprising a temperature sensor on a surface of said balloon.

14. A method for endometrial ablation, comprising
   (a) providing an endometrial ablation device which comprises an inflatable balloon and two ablation probes contained within an applicator;
   (b) inserting said applicator through a cervix into a cavity of a uterus;
   (c) pushing said balloon and said cryoprobes from said inserted applicator into said uterine cavity;
   (d) inflating said balloon so that said balloon contacts the endometrium of said uterus;
   (e) advancing said cryoprobes into cornuae of said uterus;
   (f) cooling said balloon to treat endometrial tissue of said uterine cavity, and cooling said cryoprobes to treat endometrial tissue of said cornuae;
   (g) deflating said balloon;
   (h) retracting said cryoprobes and said balloon into said applicator; and
   (i) extracting said applicator, containing said balloon and said cryoprobes, from said uterus.

15. The method of claim 14, wherein said inflatable balloon is transparent.

16. The method of claim 15, further comprising inserting a viewing optic of a hysteroscope into said transparent balloon when said transparent balloon is inserted in said uterine cavity.

17. The method of claim 16, further comprising observing endometrial tissue through said transparent balloon.

18. The method of claim 16, further comprising observing at least one of said cryoprobes through said hysteroscope while guiding said observed cryoprobe towards and into a uterine cornua.

19. The method of claim 16, further comprising utilizing said hysteroscope to assess condition of endometrial tissue subsequent to cooling of said tissue by said endometrial ablation device.

* * * * *